US006248896B1

(12) United States Patent
Nolte et al.

(10) Patent No.: US 6,248,896 B1
(45) Date of Patent: *Jun. 19, 2001

(54) PROCESS FOR THE PREPARATION OF DITHIAZOLYL DISULFIDES

(75) Inventors: Wilfried Nolte, Odenthal; Heinrich Königshofen, Bergisch Gladbach; Adolf Sicheneder, Hohenlockstedt, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/627,271

(22) Filed: Jul. 28, 2000

Related U.S. Application Data

(62) Division of application No. 09/453,971, filed on Dec. 3, 1999, now Pat. No. 6,124,467.

(30) Foreign Application Priority Data

Dec. 8, 1998 (DE) ............................................. 198 56 439

(51) Int. Cl.⁷ .................................................. C07D 417/12
(52) U.S. Cl. ............................................ 548/158; 548/186
(58) Field of Search ..................................... 548/158, 186

(56) References Cited

U.S. PATENT DOCUMENTS

| 1,908,935 | 5/1933 | Tschunkur et al. | |
|---|---|---|---|
| 2,119,131 | 5/1938 | Gracia | 260/16 |
| 3,062,825 | 11/1962 | Hardman et al. | 260/306.5 |
| 3,654,297 | 4/1972 | Goulandris | 260/306.5 |
| 3,925,401 | 12/1975 | Janin | 260/306.5 |
| 4,307,236 | 12/1981 | Zengel et al. | 548/158 |
| 6,124,467 | * 9/2000 | Nolte et al. | 548/158 |

FOREIGN PATENT DOCUMENTS

| 2743629 | 3/1978 | (DE) . |
| 2944225 | 5/1981 | (DE) . |
| 3930145 | 3/1991 | (DE) . |
| 1379871 | 1/1975 | (GB) . |

OTHER PUBLICATIONS

Encyclopedia of Polymer Science and Engineering, vol. 17,(date unavailable) pp. 666–698 Vulcanization.

Kirk–Othmer, Encyclopedia of Polymer Science & Technology, vol. 12, (month unavailable) 1970, p. 262, Helium––Group Gases.

Ullmanns Encyclopedia of Industrial Chemistry, 5th Ed., vol. A26, (date unavailable) pp. 773–778, Alkyl Sulfides, Disulfides and Polysulfides.

Encyclopedia of Polymer Science Engineering, vol. 4, (date unavailable) pp. 66–67, Compounding.

* cited by examiner

*Primary Examiner*—Laura L. Stockton
(74) *Attorney, Agent, or Firm*—Joseph C. Gil; Noland J. Cheung

(57) ABSTRACT

The invention relates to a new process for the preparation of dithiazolyl-(2,2')-disulfides by oxidation of 2-mercaptothiazoles, to the dithiazolyl-(2,2')-disulfides that can be obtained in this way, and to the use thereof.

4 Claims, No Drawings

PROCESS FOR THE PREPARATION OF DITHIAZOLYL DISULFIDES

This application is a divisional application of Ser. No. 09/453,971, filed Dec. 3, 1999 now U.S. Pat. No. 6,124,467.

FIELD OF THE INVENTION

The invention relates to a new process for the preparation of dithiazolyl-(2,2')-disulfides by oxidation of 2-mercaptothiazoles, in particular, the preparation of dibenzothiazyl disulfide from 2-mercaptobenzothiazole, to the dithiazolyl-(2,2')-disulfides that can be obtained in this way, and to the use thereof as vulcanization accelerators.

BACKGROUND OF THE INVENTION

In the technical preparation of the dibenzothiazyl disulfides by oxidation of 2-mercaptobenzothiazoles, use has been made hereto of various oxidizing agents (Ullmanns Encyclopedia of Industrial Chemistry, 5th Ed., Vol. A-26, pp 773–778, VCH, Weinheim, Basel, Cambridge, N.Y., Tokyo, 1995). For instance, the reaction with sodium chlorate and sodium-nitrite solution in hydrochloric medium at 30° C. is the state of the art. This process, however, is burdened with a number of disadvantages. The consumption of mineral acid is very high (3 moles HCl per mole 2-mercaptobenzothiazole), and large quantities of by-products are formed. Furthermore it is known to carry out the oxidation of the 2-mercaptobenzothiazole by means of nitrous acid. According to the process disclosed in U.S. Pat. No. 1,908,935, 2-mercaptobenzothiazole is suspended in water, a water-soluble nitrite is added and the oxygen or an oxygen-containing gas such as air is passed through the reaction mixture. At the same time, a mineral acid which releases nitrous acid from the nitrite is added. In the case of the process according to U.S. Pat. No. 2,119,131 and U.S. Pat. No. 3,062,825, stoichiometric quantities of nitrite are employed as the sole oxidizing agent. By this means, a quicker and more complete reaction is achieved. These oxidation processes are, likewise, disadvantageous to the extent that, here too, the consumption of mineral acid is very high, and salts, as well as nitrogen oxides, accumulate in large quantities as by-products.

Chlorine has also already been employed as an oxidizing agent (Kirk-Othmer, Encyclopedia of Polymer Science and Technology (1970), Vol. 12, p 262). In this case, however, it is a matter of a complicated reaction with critical reaction conditions, in the course of which large quantities of over oxidized secondary products frequently accumulate. According to DE 23 09 584, for the purpose of increasing the product yield and diminishing the quantity of excess chlorine that is required for sufficient oxidation, separate currents of an aqueous solution consisting of an alkali-metal salt of mercaptobenzothiazole, an aqueous solution of an alkali-metal hydroxide and gaseous chlorine are caused to react with one another continuously at 20 to 75°, with vigorous stirring, beneath the surface of the liquid, whereby the pH value and the redox potential of the aqueous mixture are maintained by regulating the influx of the aqueous hydroxide solution and of the gaseous chlorine at pH 7 to 10 and at a redox potential of −150 to 250 mV. This process also requires very careful control in order to prevent further oxidation of the dibenzothiazyl disulfide to benzothiazyl-2-sulfinate and benzothiazyl-2-sulfonate. The process is also disadvantageous for the reason that large quantities of alkali hydroxide are consumed and large quantities of common salt are formed as a by-product.

Hydroperoxides such as hydrogen peroxide, alkali hydroperoxides and aralkyl hydroperoxides have likewise already been employed as oxidizing agents in the preparation of dibenzothiazyl disulfide (eg, DE 2,349,314).

The disadvantage, which is common to all the aforementioned oxidation processes is the requirement of comparatively expensive oxidizing agents and acids, bases or other auxiliary substances, and unusable by-products or secondary products also arise in some cases.

A process of the electrolytic oxidation of 2-mercaptobenzene to form dibenzothiazyl disulfide is also disclosed in DE 2,743,629.

There have also already been investigations as to whether the oxidation of 2-mercaptobenzothiazole to dibenzothiazyl disulfide can be carried out with oxygen as the sole oxidizing agent. With the process according to U.S. Pat. No. 3,654,297, this is possible if a cobalt phthalocylamine sulfate, disulfonate, trisulfonate or tetrasulfonate or mixtures of the same is employed as catalyst and the oxidation is carried out in an organic solvent that contains less than 15 wt. % water at temperatures from 50 to 80° C. (cf. also Su 575 348; Chem. Abstr. 88 (1978), 89657 g). The production and industrial use of this catalyst, however, are problematic.

Finally, DE 2,355,897 shows the performing of the oxidation of the 2-mercaptobenzothiazoles to dibenzothiazyl disulfides by joint use of oxygen or an oxygen-containing gas and iron chloride, in particular iron(III) chloride, in a saturated aliphatic alcohol with 1 to 10 carbon atoms at temperatures between 0 and 150° C. However, this catalyst results in a satisfactory rate of reaction only when it is used in a relatively large quantity, namely in a ratio of 0.8 to 1.5 mol per mol 2-mercapto-benzothiazole. The major disadvantage of this process, however, is that during the reaction, the iron precipitates out in the form of basic salts and the dibenzothiazyl disulfide that can be obtained is strongly contaminated with iron. A product obtained in this way cannot be used as a vulcanizing agent, for example, without elaborate purification.

According to DE 2,944,225 and DE 3,118,298, heavy-metal catalysts and amines are employed as a catalyst mixture. It is also possible for the amine to be replaced by ammonia.

The use of toxic heavy-metal catalysts such as Cd is problematic from ecological points of view; the residues of the toxic heavy-metal catalysts are, in addition, to be found in the final product or removed in an elaborate manner.

SUMMARY OF THE INVENTION

There is still, therefore, a need to create a process for the catalytic oxidation of 2-mercaptobenzothiazoles by means of oxygen or gases containing oxygen.

The present invention provides a process for the preparation of dithiazolyl-(2,2')-disulfides having the general formula

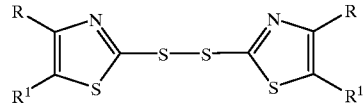

wherein

R and R$^1$ may be the same or different and each stand for hydrogen, halogen, nitro, hydroxyl or, optionally, in turn, substituted $C_1$–$C_{12}$ alkyl or $C_1$–$C_{12}$ alkoxyl or $C_6$–$C_{12}$ cycloalkyl or $C_6$–$C_{12}$ aryl or jointly form the residue

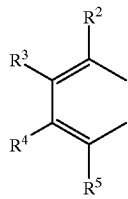

wherein $R^2$, $R^3$, $R^4$ and $R^5$ have the same meaning as R and $R^1$, characterized in that an appropriately substituted 2-mercaptothiazole is oxidized with oxygen or an oxygen-containing gas in the presence of a solvent and a tertiary amine and an organic iron compound.

DETAILED DESCRIPTION OF THE INVENTION

The present invention relates to process for the preparation of dithiazolyl-(2,2')-disulfides having the general formula

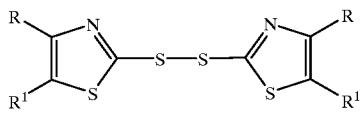

wherein

R and $R^1$ may be the same or different and each stand for hydrogen, halogen, nitro, hydroxyl or, optionally, in turn, substituted $C_1$–$C_{12}$ alkyl or $C_1$–$C_{12}$ alkoxyl or $C_6$–$C_{12}$ cycloalkyl or $C_6$–$C_{12}$ aryl or jointly form the residue

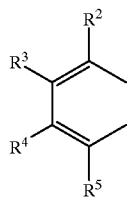

wherein $R^2$, $R^3$, $R^4$ and $R^5$ have the same meaning as R and $R^1$, characterized in that an appropriately substituted 2-mercaptothiazole is oxidized with oxygen or an oxygen-containing gas in the presence of a solvent and a tertiary amine and an organic iron compound.

In the embodiment where the residues R, $R^1$, $R^2$, $R^3$, $R^4$ and $R^5$ stand for halogen, a halogen is defined as fluorine, chlorine, bromine or iodine; chlorine and bromine are preferred.

$C_1$–$C_{12}$ alkyls are to be understood to mean all linear or branched alkyl residues with 1 to 12 C, such as methyl, ethyl, n-propyl, i-propyl, n-butyl, i-butyl, t-butyl, n-pentyl, i-pentyl, neopentyl and hexyl, which, in turn, may again be substituted. By way of substituents in this connection, halogen, nitro, hydroxyl or also $C_1$–$C_{12}$ alkyl or alkoxy, as well as $C_6$–$C_{12}$ cycloalkyl or $C_6$–$C_{12}$ aryl, come into consideration, such as benzoyl, trimethylphenyl, ethylphenyl, chloromethyl, chloroethyl and nitromethyl.

$C_1$–$C_{12}$ alkoxyl is to be understood to mean all linear or branched alkoxyl residues with 1 to 12 C atoms which are known to a person skilled in the art, such as methoxy, ethoxy, n-propoxy, i-propoxy, n-butoxy, i-butoxy, t-butoxy, n-pentoxy, i-pentoxy, neopentoxy and hexoxy, which, in turn, may again be substituted. By way of substituents in this connection, halogen, nitro, hydroxyl or also $C_1$–$C_{12}$ alkyl or alkoxyl, as well as $C_6$–$C_{12}$ cycloalkyl or $C_6$–$C_{12}$ aryl, come into consideration.

$C_6$–$C_{12}$ cycloalkyl is to be understood to mean all mononuclear or polynuclear cycloalkyl residues with 6 to 12 C atoms, such as cyclohexyl, cycloheptyl, cyclo-octyl and cyclononyl, which, in turn, may again be substituted. By way of substituents in this connection, halogen, nitro, hydroxyl or also $C_1$–$C_{12}$ alkyl or alkoxyl, as well as $C_6$–$C_{12}$ cycloalkyl or $C_6$–$C_{12}$ aryl, come into consideration, such as methylcyclohexyl, chlorocyclohexyl and nitrocyclohexyl.

$C_6$–$C_{12}$ aryl is to be understood to mean all mononuclear or polynuclear aryl residues with 6 to 12 C atoms, such as phenyl, naphthyl, which, in turn, may again be substituted. By way of substituents in this connection, halogen, nitro, hydroxyl or also $C_1$–$C_{12}$ alkyl or alkoxyl, as well as $C_6$–$C_{12}$ cycloalkyl or $C_6$–$C_{12}$ aryl, come into consideration, such as bromophenyl, chlorophenyl, toloyl and nitrophenyl.

The residues R, $R^1$, $R^2$, $R^3$, $R^4$ and $R^5$ preferably represent hydrogen, methyl, ethyl, propyl, t-butyl, methoxy, ethoxy, cyclohexyl, benzoyl, methoxy, ethoxy, phenyl, naphthyl, chlorophenyl, toloyl and nitrophenyl.

Dithiazolyl-(2,2')-disulfides are used as vulcanizing agents for rubber. The process according to the present invention is important in particular for the preparation of dibenzothiazolyl-(2,2')-disulfide, the most important representative of this class of compounds. However, it is suitable just as successfully in connection with the preparation of further compounds of this type. For the preferred preparation of dibenzothiazolyl-(2,2')-disulfide, 2-mercaptobenzothiazole finds application by way of initial substance. Examples of other 2-mercaptothiazoles that are suitable as initial substances for the preparation of further dithiazolyl-(2,2')-disulfides of the general formula (I) are, inter alia, the compounds named in DE 23 55 897, inter alia 2-mercaptothiazole
2-mercapto-4-methylthiazole
2-mercapto-4-ethylthiazole
2-mercapto-4n-propylthiazole
2-mercapto-4n-butylthiazole
2-mercapto-4,5-dimethylthiazole
2-mercapto-4,5-di-n-butylthiazole
2-mercapto-4-phenylthiazole
2-mercapto-5-chloro4-phenylthiazole
2-mercapto-4-p-bromophenylthiazole
2-mercapto-4-m-nitrophenylthiazole
2-mercapto-4-m-chlorophenylthiazole
2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole
2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole 2-mercapto-5-chloro-6-methoxybenzothiazole
2-mercapto-5-chloro-4-nitrobenzothiazole
2-mercapto-5-chloro-6-nitrobenzothiazole
2-mercapto-4,5-dichlorobenzothiazole
2-mercapto-4,7-dichlorobenzothiazole
2-mercapto-5-nitrobenzothiazole
2-mercapto-6-nitrobenzothiazole
2-mercapto-4-phenylbenzothiazole
2-mercapto-naphthothiazole
2-mercapto-6-hydroxybenzothiazole By way of an oxidizing agent, use is made of oxygen or a gas containing oxygen, preferably air. Conversion and selectivity increase with increasing oxygen pressure or partial pressure. In general, in the process according to the present invention, the pressure or partial pressure of oxygen lies in the range from 0.1 to 150 bar. For economic reasons, pressures or partial pressures of oxygen from 2 to 10 bar are preferably used, in particular from 3 to 8 bar.

All oxidatively stable organic solvents are suitable by way of solvent. Examples of these are alcohols, dimethylformamide, benzene, toluene and chlorobenzene. Suitable alcohols are, for example, aliphatic alcohols with 1 to 10 carbon atoms, in particular methanol, ethanol, propanol, isopropanol, n-butanol, sec.-butanol, tert.-butanol, pentanol, hexanol, heptanol and octanol. Toluene and isopropanol are preferably used. Another suitable solvent is water, which is employed in a particularly preferred manner by way of solvent in the process according to the preset invention. The concentration of the solvent is not critical. In general, the quantity of solvent lies in the range from 200 to 1,200 wt.-%, relative to 2-mercaptothiazole employed. Larger quantities of solvent are to be avoided for economic reasons, since in these cases, larger quantities of tertiary amine are also needed.

Suitable tertiary amines are aliphatic, cycloaliphatic, aromatic and heterocyclic amines such as, for example, trimethylamine, triethylamine, tri-n-propylamine, tri-n-butylamine, n-octyldimethylamine, diisopropylethylamine, propyidimethylamine, ethyidimethylamine, isopropyidimethylamine, butyldimethylamine, pyridine, N-methyl pyridine, N-methyl pyrrolidine, 2,4,6-trimethyl pyridine, 2,3,4,5-tetramethyl pyridine, 2,3,4,5,6-pentamethyl pyridine, dimethylaniline, dimethylbenzylamine (DMBA), 4-methylamino pyridine and 1,4-diazabicyclo-(2,2,2)-octane. Preferred tertiary amines are trimethylamine, triethylamine, tri-n-propylamine, tri-n-butylamine and dimethylbenzylamine. Particularly preferred is dimethylbenzylamine.

The named tertiary amines are not all equally effective. As a rule, the catalytic effectiveness is greater, the higher the basicity of the amine. But, in addition, steric effects can also have an influence on the catalytic effectiveness of the tertiary amine.

The quantity of the tertiary amine can be varied within a wide range. Catalytic quantities are already sufficient. With increasing quantities of the tertiary amine, the catalytic effectiveness thereof also increases, depending more on the concentration of the tertiary amine in the reaction mixture and less on the quantitative ratio of tertiary amine to the 2-mercaptothiazole employed. The tertiary amine is preferably employed in quantities from 0.1 to 20 wt.-%, relative to the reaction mixture.

The tertiary amines to be used in accordance with the invention may be employed both on their own and jointly with a hydroxide compound.

By way of hydroxide compound, alkali-metal and alkaline-earth-metal hydroxides and ammonium hydroxide come into consideration, such as lithium hydroxide, sodium hydroxide, potassium hydroxide, magnesium hydroxide and calcium hydroxide.

Preferred are sodium hydroxide, potassium hydroxide and ammonium hydroxide.

The quantities of hydroxide compound that are used lie in the range from 0.001 to 5 mol per mol thiazole, preferably 0.05 to 2 mol, particularly preferred 0.09 to 1.5 mol.

Suitable by way of organic iron compound are all iron complexes, in which the iron is complexed with a high complex formation constant, known to a person skilled in the art, such as iron(III) haemin, iron hemiporphyrazine (Fe hemi), iron phthalocyanine; iron hemiporphyrazine is preferably employed.

The quantities of organic iron compound that are used lie in the range from 0.01 to 1,000 mmol per mol thiazole, preferably 0.1 to 100 mmol, particularly preferred 0.5 to 10 mmol.

The reaction temperature amounts to 0 to 150° C., preferably 20 to 90° C. and in particular, 60 to 80° C. At lower temperatures the rate of reaction declines; at higher temperatures the selectivity of the reaction diminishes.

The reaction-time under the stated preferred pressure and temperature conditions amounts, as a rule, to 0.5 to 30 hours.

The process according to the present invention is implemented in a simple manner by the oxygen or the gas containing oxygen being passed, under the stated pressure and temperature conditions, into or through the solution consisting of the 2-mercaptothiazole, the solvent, organic iron compound and tertiary amine. Since, in certain circumstances, unreacted 2-mercaptothiazole remains dissolved in the solvent, processing of the reaction mixture takes a very simple form. The reaction product, which has precipitated out, is filtered off or centrifuged off, the mother liquor is mixed with fresh 2-mercaptothiazole and conducted in a circuit. Depending on how high the initial concentration of the organic iron compound was, fresh organic iron compound has to be added after a certain number of reaction cycles. In addition, the water of reaction which has arisen in the course of the reaction should preferably be discharged from the mother liquor when its content—relative to mother liquor—amounts to more than 10 wt.-%.

Practically quantitative yields and selectivities of more than 99% are achieved with the process according to the invention. The dithiazolyl-(2,2')-disulfides that can be obtained are distinguished by high purity; they may be employed without further purification, for example they may be employed directly as vulcanizing agents for rubber. In comparison with the known processes, in which a 2-mercaptobenzothiazole is likewise oxidized by means of oxygen, the process according to the present invention is distinguished in that simple and inexpensive catalysts are used in very small quantities and in that these catalysts can be conducted in a circuit with the mother liquor without their activity noticeably falling off and without toxic heavy metals having to be employed and then removed from the product.

The dithiazolyl-(2,2')-disulfides that can be prepared in accordance with the present invention are outstandingly suitable as vulcanization accelerators in sulfurous rubber mixtures. Particularly suited is dibenzothiazyl disulfide.

The sulfurous rubber mixtures may be prepared and vulcanized in conventional manner, as described in detail in, for example, Encyclopedia of Polymer Science and Engineering, Vol. 4, p 66 ff (Compounding) and Vol. 17, p 666 ff (Vulcanization).

The sulfurous rubber mixtures may, of course, also contain other rubber auxiliary products, such as reaction accelerators, age-resisters, heat stabilizers, light-screening agents, anti-ozonants, processing aids, elasticizers, tackifiers, foaming agents, dyestuffs, pigments, waxes, extenders, organic acids, retarders, metal oxides and also activators such as triethanolamine, polyethylene glycol, hexanetriol, which are known and conventional in the rubber industry. The rubber auxiliaries are admixed in conventional quantities and conform to the intended purpose in the given case. Conventional quantities are, for example, quantities from 0.1 to 50 wt. %, relative to the total quantity of the rubber employed. With a view to improving the thermal stability and stability in storage, known phenolic, amine-type, sulfurous or phosphorous age-resisters are preferably added. These are described more fully in, for example, Ullmanns Enzyklopedie der technischen Chemie, Volume 8, p 19 ff.

In addition to the rubber auxiliary products previously mentioned, the known crosslinkers, such as sulfur, sulfur donors or peroxides, can be added to the rubber mixtures according to the invention. The aforementioned crosslinkers are conventionally employed in quantities from 0.1 to 10 wt. %, preferably 0.1 to 5 wt. %, relative to the total quantity of the rubber employed in the given case.

Vulcanization of the rubber mixtures according to the present invention can be carried out at conventional temperatures from 100 to 200° C., preferably 130 to 180° C. (optionally under pressure of 10 to 200 bar).

Blending of the rubbers with the other aforementioned rubber auxiliary products, crosslinkers and accelerators can be carried out in conventional manner with the aid of suitable mixing units such as rollers, internal mixers and mixing extruders.

EXAMPLES

Example 1

600ml water, 83.6 g (0.5 mol) 2-mercaptobenzothiazole (MBT), 13.5 g (0.1 mol) dimethylbenzylamine (DMBA) and 0.3 g (0.5 mmol) iron hemiporphyrazine at a partial oxygen pressure amounting to 6 bar are submitted in an autoclave and caused to react at 60° C., with stirring. After 16.5 h of reaction, 143 g dibenzothiazyl sulfide (MBTS) are filtered off.

Example 2

600g methanol, 100.3 g (0,6 mol) MBT, 22.68 g (0.168 mol) DMBA and 0.36 g (0.6 mmol) iron hemiporphyrazine are submitted in an autoclave. Subsequently 10 to 15 l/h of air were passed through the mixture for 4 h at 60° C. 180 g MBTS were obtained, which could be filtered off.

Example 3

Working proceeded in a manner analogous to Example 2, but, instead of DBMA, 17 g (0.168 mol) triethylamine were employed. 98 g MBTS were obtained, which could be filtered off.

Example 4

Working proceeded in a manner analogous to Example 3, but, instead of iron hemiporphyrazine, 0.34 g (0.6 mmol) iron phthalocyanine was employed. 33.8 g MBTS were obtained, which could be filtered off.

Example 5

167 g (1 mol) MTB, 1,500 ml water, 60.75 g (0.45 mol) DBMA and 8 g (0.2 mol) NaOH were submitted in an autoclave; the pH amounted to 8.3. Subsequently 10 to 15 l/h of air were passed through the mixture for 3.5 h at 60° C. 46.5 g MBTS were obtained, which could be filtered off.

Example 6

Working proceeded in a manner analogous to Example 5, but addition of NaOH was dispensed with, and instead of this the quantity of DMBA was increased to 837 g (6.2 mol); the pH amounted to 7.8. 37.2 g MBTS were obtained, which could be filtered off.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a dithiazolyl-(2,2')-disulfide of the general formula

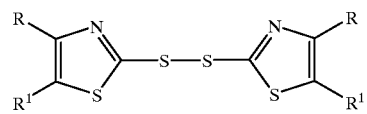

wherein

R and $R^1$ may be the same or different and each represents hydrogen, halogen, nitro, hydroxyl or optionally substituted $C_1$–$C_{12}$ alkyl, $C_1$–$C_{12}$ alkoxyl, $C_6$–$C_{12}$ cycloalkyl, $C_1$–$C_{12}$ aryl or jointly form the residue

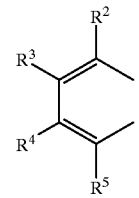

wherein $R^2$, $R^3$, $R^4$ and $R^5$ have the same meaning as R and $R^1$, consisting essentially of the step of oxidizing a substituted 2-mercaptothiazole with oxygen or an oxygen-containing gas in the presence of a solvent wherein said solvent is not water, and a tertiary amine and also an organic iron compound wherein said organic iron compound is iron hemiporphyrazine.

2. A process according to claim 1, wherein said tertiary amine is dimethylbenzylamine.

3. A process according to claim 1, wherein said tertiary amine is employed in quantities in the range from 0.001 to 5 mol per mol thiazole.

4. A process according to claim 1, wherein said organic iron compound is employed in quantities in the range of from 0.01 to 1,000 mmol per mol thiazole.

* * * * *